(12) United States Patent
Mishra et al.

(10) Patent No.: US 9,108,924 B2
(45) Date of Patent: Aug. 18, 2015

(54) PROCESS FOR THE PREPARATION OF BENDAMUSTINE HYDROCHLORIDE

(71) Applicant: FRESENIUS KABI ONCOLOGY LIMITED, New Delhi (IN)

(72) Inventors: Bhuwan Bhaskar Mishra, Haryana (IN); Nikunj Shambhubhai Kachhadia, Haryana (IN); Vinod Singh Tomar, Haryana (IN); Saswata Lahiri, Haryana (IN)

(73) Assignee: Fresenius Kabi Oncology Limited, New Delhi (IN)

( * ) Notice: Subject to any disclaimer, the term of this patent is extended or adjusted under 35 U.S.C. 154(b) by 47 days.

(21) Appl. No.: 13/623,536

(22) Filed: Sep. 20, 2012

(65) Prior Publication Data

US 2014/0121383 A1    May 1, 2014

(30) Foreign Application Priority Data

Sep. 26, 2011  (IN) ............... 2795/DEL/2011

(51) Int. Cl.
*C07D 235/16* (2006.01)
(52) U.S. Cl.
CPC .................... *C07D 235/16* (2013.01)
(58) Field of Classification Search
None
See application file for complete search history.

(56) References Cited

U.S. PATENT DOCUMENTS

| 2006/0128777 A1 | 6/2006 | Bendall et al. |
| 2006/0159713 A1 | 7/2006 | Brittain et al. |
| 2010/0234435 A1* | 9/2010 | Bhattacharya et al. ........ 514/364 |

FOREIGN PATENT DOCUMENTS

| DE | 34727 | 12/1964 |
| DE | 159877 | 4/1983 |
| WO | 2009/120386 | 10/2009 |
| WO | 2010/036702 | 4/2010 |
| WO | 2010/042568 | 4/2010 |
| WO | 2011/079193 | 6/2011 |
| WO | WO-2012/007966 A2 * | 1/2012 |

OTHER PUBLICATIONS

Leopoldo et al., Journal of Pharmacy and Pharmacology, 2006, 58, pp. 209-218.*
Coggiola et al., Bioorganic & Medicinal Chemistry Letters, 2005, 15, pp. 3551-3554.*
Ghosh et al., Tetrahedron Letters, 2010, 51, pp. 3177-3180.*
Rosen et al., ACS Medical Chemistry Letters, Oct. 5, 2010, 1(9), pp. 526-529.*
Emmerson et al., Organic & Biomolecular Chemistry, 2003, 1(21), pp. 3826-3838.*
Hilal, Estimation of Hydrolysis Rate Constants of Carboxylic Acid Ester and Phosphate Ester Compounds in Aqueous Systems from Molecular Structure by SPARC, EPA/600/R-06/105, Sep. 2006.*
Disclosed Anonymously, "Process for Preparing 4-[5-[BIS(2-Chloroethyl)Amino]-1-Methylbenzimidazol-2-YL) Butanoic Acid Intermediate," IP.com, Jul. 13, 2009, pp. 1-4.
Gao et al., "Synthesis of Bendamustine," Chinese Journal of New Drugs, 2007, vol. 16, No. 23, 1960-1961. (English translation included.).
Ozegowski et al., "W-[bis-(chloroethyl)-amino-benzimidazolyl(2)]-propionic or -butyric acids as potential cytostatic agents," Journal für Praktische Chemie, Series 4, vol. 20, 1963 (178-186).
Ozegowski et al., "IMET 3393, γ-[1-methyl-5-bis-(β-chloroethyl)-aminobenzimidazolyl-(2)]-butyric acid hydrochloride, a new cytostatic drug from the benzimidazole mustard gas series," Journal of Abstracts and Reviews for Pharmacy, Pharmacotherapy, and Laboratory Diagnostics , 110 ( 1971 ), No. 10, pp. 1013-1019. (English translation included.).

* cited by examiner

*Primary Examiner* — Laura L. Stockton
(74) *Attorney, Agent, or Firm* — Occhiuti & Rohlicek LLP

(57) ABSTRACT

The present invention relates to an improved process for the synthesis of bendamustine, in particular, bendamustine hydrochloride of the formula (VI) and its intermediate 1-methyl-5-[bis(2-chloroethyl)amino]-1H-benzimidazol-2-yl] lithium butanoate of formula (V), both having a purity of ≥99%, which is simple, convenient, economical, does not use hazardous chemicals and is industrially viable.

27 Claims, 2 Drawing Sheets

PROCESS FOR THE PREPARATION OF BENDAMUSTINE HYDROCHLORIDE

FIELD OF THE INVENTION

The present invention relates to an improved process for the preparation of bendamustine, in particular, bendamustine hydrochloride and its intermediates, both having a purity of ≥99%, which is simple, convenient, economical and industrially viable.

BACKGROUND OF THE INVENTION

Bendamustine hydrochloride, 4-[5-[Bis(2-chloroethyl) amino]-1-methyl-2-benzimidazolyl]butyric acid hydrochloride, of the formula (VI):

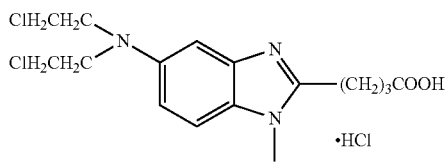

(VI)

was initially synthesized in 1963 in the German Democratic Republic (GDR) and was available there from 1971 to 1992, as the hydrochloride salt, under the trade name Cytostasan®. Since then, it has been marketed in Germany under the trade name Ribomustin®. Bendamustine hydrochloride for injection is available in the United States under the tradename Treanda®. Bendamustine hydrochloride is an alkylating agent that is approved for the treatment of non-Hodgkin's lymphoma, multiple myeloma and chronic lymphocytic leukemia.

Bendamustine hydrochloride is a benzimidazole analog. While bendamustine has been demonstrated as efficacious, it is known to be unstable, especially in aqueous solutions, leading to the formation of non-bendamustine products (i.e. "degradation impurities"). This leads to technical difficulties in its preparation and administration. In light of its instability in aqueous solution, bendamustine is supplied as a lyophilized cake of bendamustine hydrochloride salt. US2006/159713, US 2006/128777 and WO2010/036702 disclose various impurities of bendamustine hydrochloride which are as follows:

(HP1)

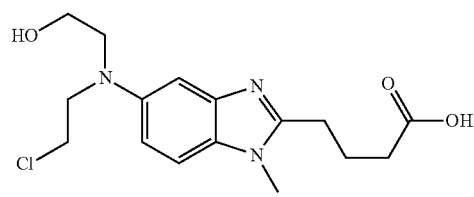

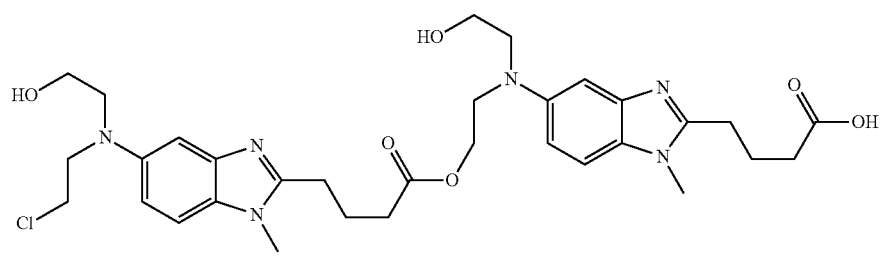

(BM1 dimer)

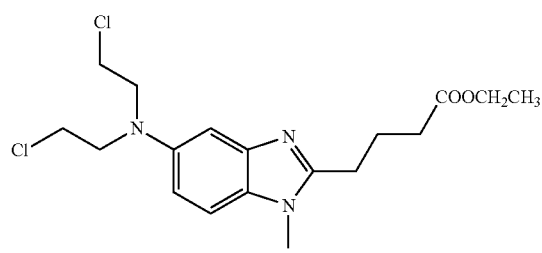

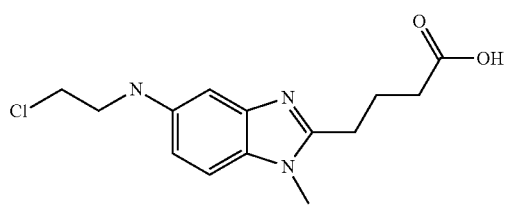

(DCE)

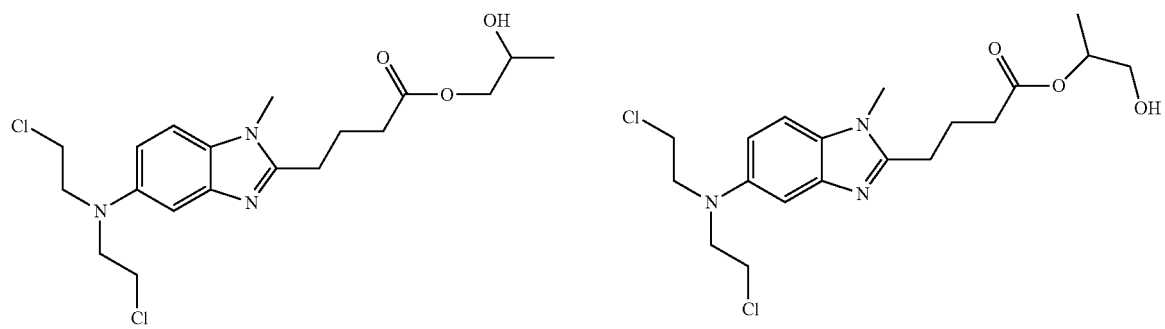

Jena et al. were the first to disclose the synthesis of bendamustine hydrochloride in German (GDR) Patent No. 34727. Krueger et al., in German (GDR) Patent No. 159877, recite a method as summarized in scheme-1 for the synthesis of bendamustine hydrochloride comprising the reaction of the 4-[1-methyl-5-bis-(2-hydroxyethyl)-benzimidazolyl-2]butyric acid ethyl ester (4) (or the corresponding methyl, propyl or butyl ester) with thionyl chloride in chloroform at 0-5° C. to form 4-[1-methyl-5-bis-(2-chloroethyl)-benzimidazolyl-2] butyric acid ethyl ester (5). Excess thionyl chloride is destroyed by stirring the reaction mixture in aqueous HCl. Finally, chloroform is distilled off and stirred at 95° C. for 3 hours. The reaction mixture is partially concentrated and the residue is diluted with water and stirred up to crystallization. Further purification is done by recrystallization from water.

Scheme-1: Method disclosed by Krueger et al. in DD159877 for the synthesis of Bendamustine hydrochloride

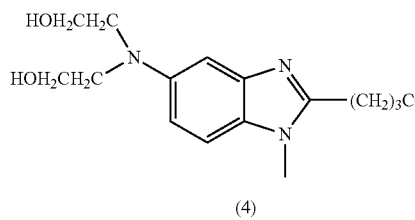

(4)

Thionyl Chloride
Chloroform

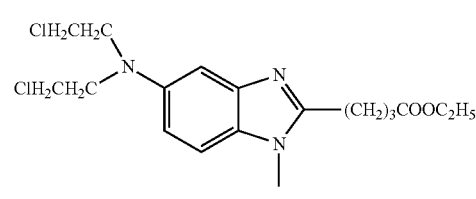

(5)

Conc. HCl,
Water

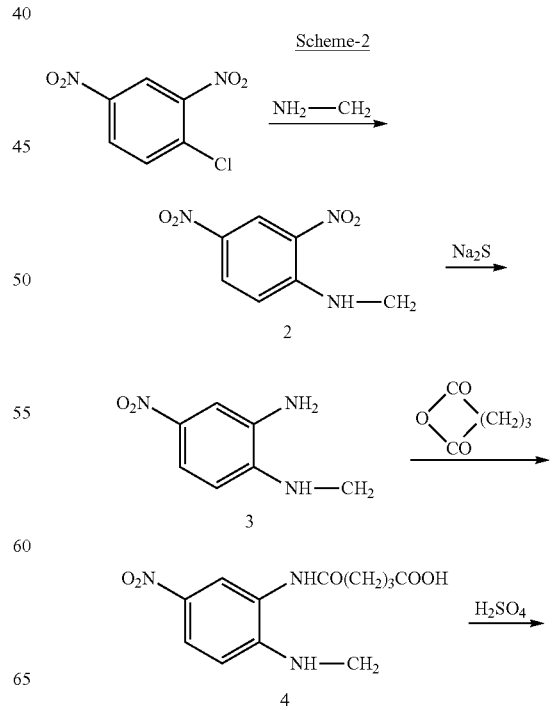

Bendamustine hydrochloride\
(6)

Ozegowski et al., in Zentralblatt fuer Pharmazie, Pharmakotherapie and Laboratoriumsdiagnostik 110 (10), 1013-1019 (1971) disclose a process for the preparation of bendamustine hydrochloride monohydrate. The Chinese journal "Chinese Journal of New Drugs", 2007, No. 23, Vol. 16, 1960-61 and *J. Prakt. Chem.* 20, 178-186 (1963) disclose another method for the synthesis of bendamustine hydrochloride monohydrate starting from 2,4-dinitrochlorobenzene as summarized in scheme-2.

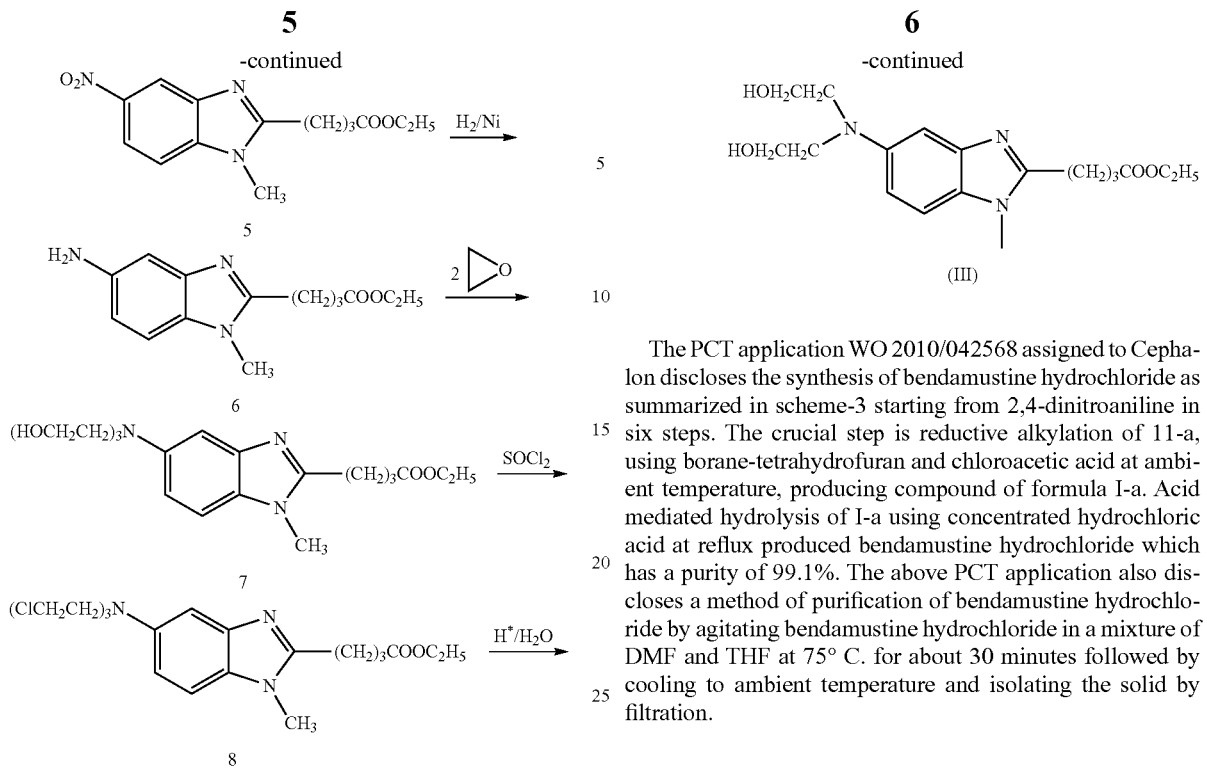

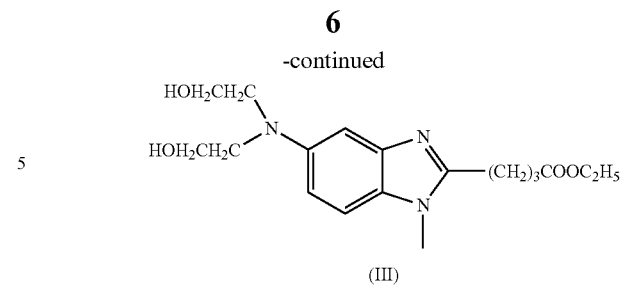

The PCT application WO 2010/042568 assigned to Cephalon discloses the synthesis of bendamustine hydrochloride as summarized in scheme-3 starting from 2,4-dinitroaniline in six steps. The crucial step is reductive alkylation of 11-a, using borane-tetrahydrofuran and chloroacetic acid at ambient temperature, producing compound of formula I-a. Acid mediated hydrolysis of I-a using concentrated hydrochloric acid at reflux produced bendamustine hydrochloride which has a purity of 99.1%. The above PCT application also discloses a method of purification of bendamustine hydrochloride by agitating bendamustine hydrochloride in a mixture of DMF and THF at 75° C. for about 30 minutes followed by cooling to ambient temperature and isolating the solid by filtration.

Scheme-3:

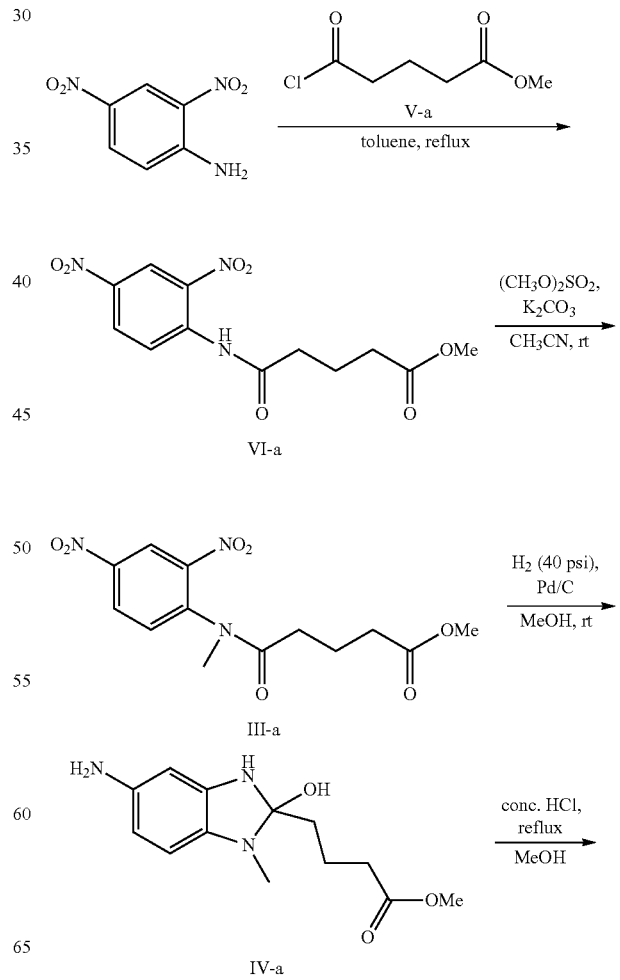

The crucial conversions are reaction of 1-methyl-2-(4'-ethyl butyrate)-5-amino]-1H-benzimidazole 6 with ethylene oxide in the presence of water, sodium acetate and acetic acid, by maintaining at 5° C. for 5 hours and overnight at 20° C. to give 4-{5-[bis-(2-hydroxy-ethyl)-amino]-1-methyl-1H-benzimidazol-2-yl}-butyric acid ethyl ester (dihydroxy ester) 7 as a jelly mass, which on chlorination using thionyl chloride in chloroform and subsequent in situ hydrolysis with concentrated HCl gave bendamustine hydrochloride. The publications also disclose a process for the recrystallization of bendamustine hydrochloride from water and the product obtained is a monohydrate with a melting point of 148-151° C.

IP.com Journal 2009, 9(7B), 21 discloses another process as shown below for the preparation of ethyl-4-[5-[bis(2-hydroxyethyl)amino]-1-methylbenzimidazol-2-yl]butanoate (III) wherein ethyl-4-(5-amino-1-methyl-1H-benzo[d]imidazol-2-yl) butanoate (II) is reacted with 2-haloethanol in the presence of an inorganic base selected from the group consisting potassium carbonate, potassium bicarbonate, sodium carbonate, and sodium bicarbonate.

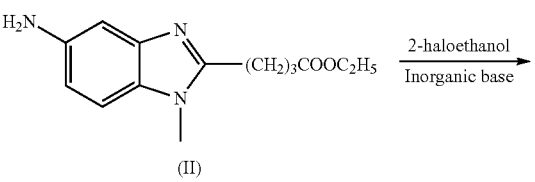

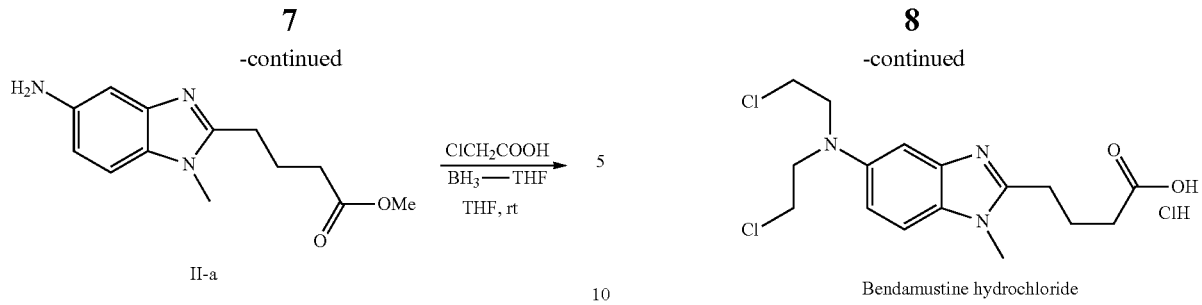

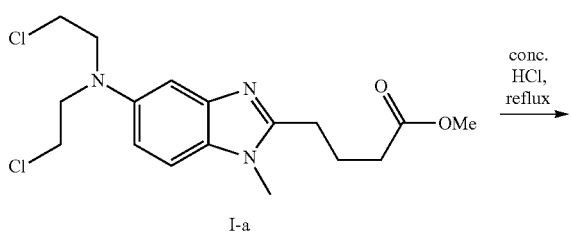

The PCT application WO 2011/079193 assigned to Dr. Reddy's Laboratories discloses the synthesis of bendamustine hydrochloride as summarized in scheme-4 starting from compound of formula (II). The crucial step is alkylation of compound of formula II with 2-haloethanol in the presence of an organic base to give a compound of formula (III), which on chlorination with a chlorinating agent affords a compound of formula (IV). Compound of formula (IV) on hydrolysis in acidic medium gives bendamustine hydrochloride. The PCT application further discloses purification of bendamustine hydrochloride using aqueous hydrochloric acid and acetonitrile.

Scheme-4:

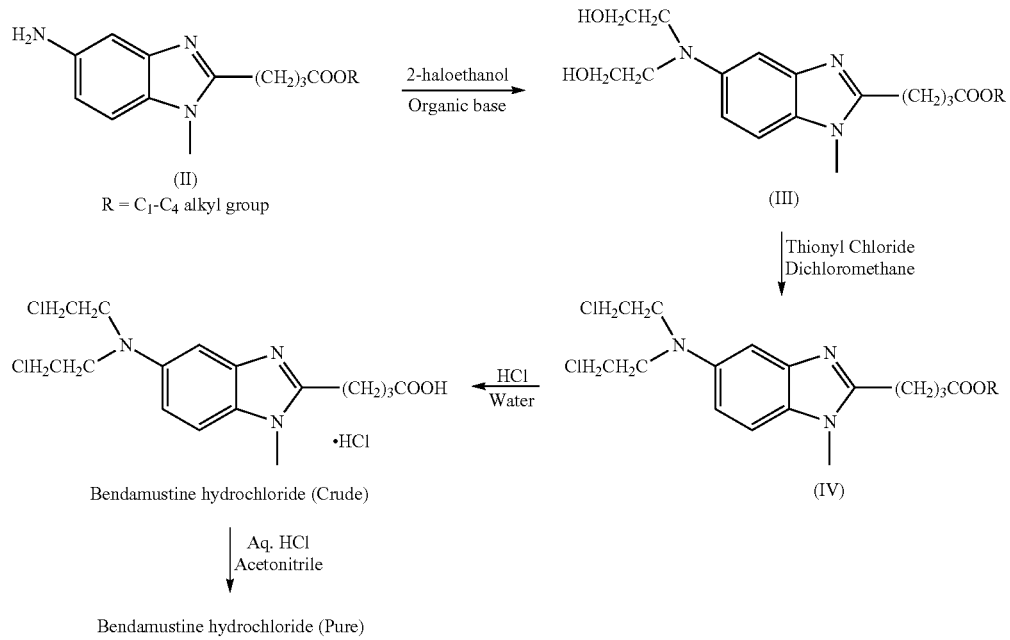

Most of the prior art processes described above involve the use of ethylene oxide for the preparation of bendamustine hydrochloride, which is often not suitable for industrial scale processes due to difficulty in handling ethylene oxide, which is shipped as a refrigerated liquid.

Further, the known processes involve the use of strongly acidic conditions and high temperatures in hydrolyzing the ethyl ester of bendamustine and subsequent in situ formation of bendamustine hydrochloride, resulting in increased levels of various process-related impurities IMP.-A (RRT-0.46), IMP.-B (RRT-1.27) and IMP.-C(RRT-1.31), whose removal is quite difficult and which makes the process less economically viable.

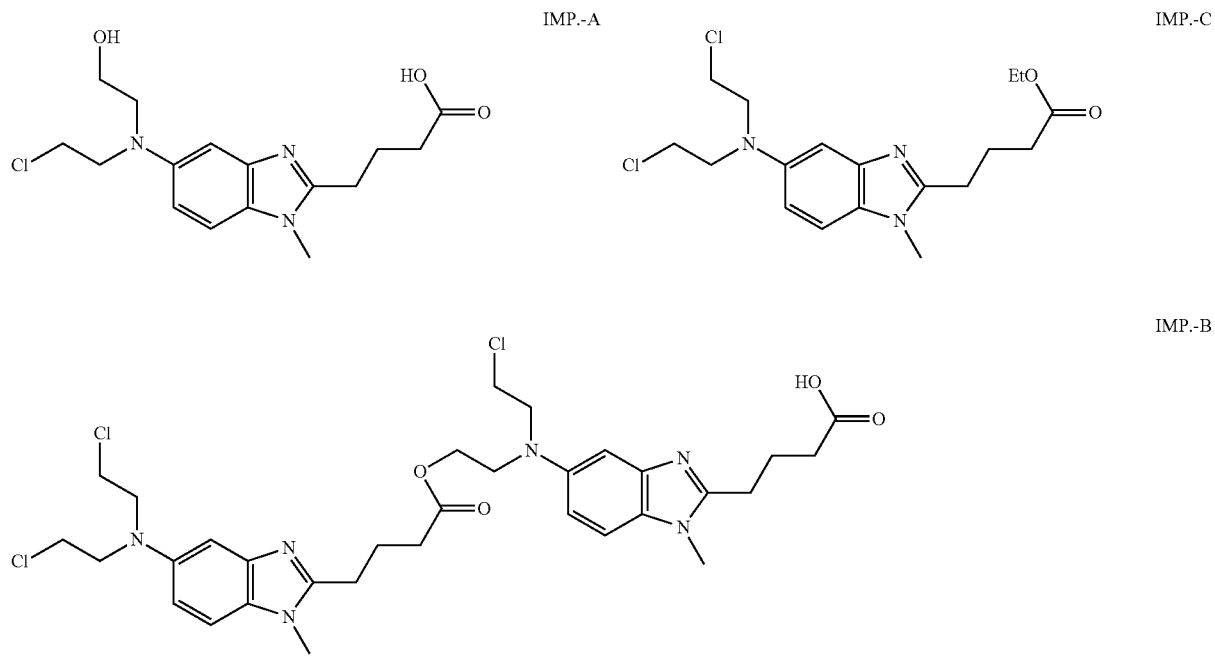

International Application Publication No. WO 2009/120386 describes various solid forms of bendamustine hydrochloride designated as bendamustine hydrochloride Form 1, bendamustine hydrochloride Form 2, bendamustine hydrochloride Form 3, bendamustine hydrochloride Form 4, amorphous bendamustine hydrochloride and mixtures thereof, as well as processes for their preparation and lyophilized compositions comprising the solid forms. According to the disclosure, the monohydrate of bendamustine hydrochloride has been prepared previously. The monohydrate has a reported melting point of 152-156° C., which is similar to that of the observed melting point of bendamustine hydrochloride Form 2.

It is known that synthetic compounds can contain extraneous compounds or impurities resulting from their synthesis or degradation. The impurities can be unreacted starting materials, by-products of the reaction, products of side reactions, or degradation products. Generally, impurities in an active pharmaceutical ingredient (API) may arise from degradation of the API itself, or during the preparation of the API. Impurities in bendamustine hydrochloride or any active pharmaceutical ingredient (API) are undesirable and might be harmful.

Regulatory authorities worldwide require that drug manufacturers isolate, identify and characterize the impurities in their products. Furthermore, it is required to control the levels of these impurities in the final drug compound obtained by the manufacturing process and to ensure that any impurities are present in the lowest possible levels, even if structural determination is not possible.

The product mixture of a chemical reaction is rarely a single compound with sufficient purity to comply with pharmaceutical standards. Side products and by-products of the reaction and adjunct reagents used in the reaction will, in most cases, also be present in the product mixture. At certain stages during processing of the active pharmaceutical ingredient, the product is analyzed for purity, typically, by HPLC, TLC or GC analysis, to determine if it is suitable for continued processing and, ultimately, for use in a pharmaceutical product. Purity standards are set with the intention of ensuring that an API is as free of impurities as possible, and, thus, is as safe as possible for clinical use. The United States Food and Drug Administration guidelines recommend that the amounts of some impurities are limited to less than 0.1 percent.

Generally, impurities are identified spectroscopically and by other physical methods, and then the impurities are associated with a peak position in a chromatogram (or a spot on a TLC plate). Thereafter, the impurity can be identified by its position in the chromatogram, which is conventionally measured in minutes between injection of the sample on the column and elution of the particular component through the detector, known as the "retention time" ("RT"). This time period varies daily based upon the condition of the instrumentation and many other factors. To mitigate the effect that such variations have upon accurate identification of an impurity, practitioners use "relative retention time" ("RRT") to identify impurities. The RRT of an impurity is its retention time divided by the retention time of a reference marker.

As is known by those skilled in the art, the management of process impurities is greatly enhanced by understanding their chemical structures and synthetic pathways, and by identifying the parameters that influence the amount of impurities in the final product.

Therefore, there remains a need for improved processes for preparing bendamustine hydrochloride, producing bendamustine hydrochloride in high yield and purity, and well-suited for use on an industrial scale. Despite the existence of various polymorphic forms of bendamustine hydrochloride, there exists a need for a simple process for the preparation of the stable form of bendamustine hydrochloride which is amenable to scale up and results in high yield and purity.

SUMMARY OF THE INVENTION

A first aspect of the present invention provides an improved process for the preparation of bendamustine hydrochloride of the formula (VI)

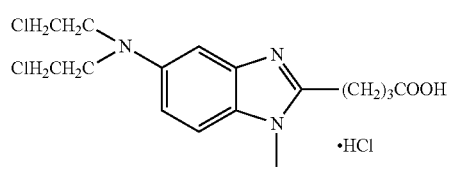
(VI)

comprising the steps of:

a) reacting a compound of the formula (II), wherein R is $C_1$-$C_6$ alkyl

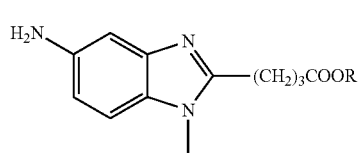
(II)

with a 2-haloethanol in the presence of a base to give a compound of formula (III);

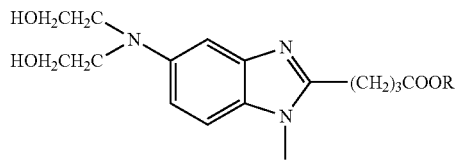
(III)

b) reacting the compound of formula (III) with a chlorinating agent to provide a compound of formula (IV);

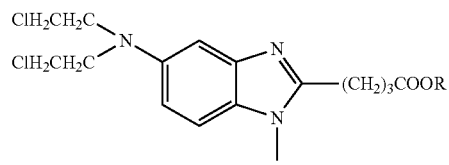
(IV)

c) hydrolyzing the compound of formula (IV) with a lithium source to give a compound of formula (V); and

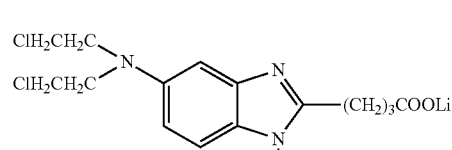
(V)

d) converting the compound of formula (V) to bendamustine or bendamustine hydrochloride of formula VI

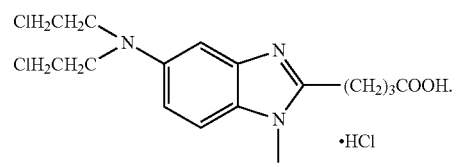
(VI)

A second aspect of the present invention provides a lithium salt of 4-[1-methyl-5-bis-(2-chloroethyl)-benzimidazolyl-2]butyric acid of formula (V)

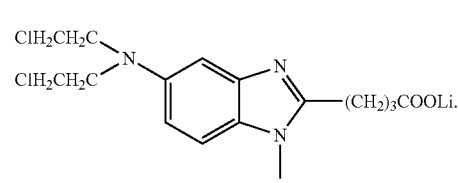
(V)

A third aspect of the present invention provides a process for the preparation of a lithium salt of 4-[1-methyl-5-bis-(2-chloroethyl)-benzimidazolyl-2]butyric acid of formula (V)

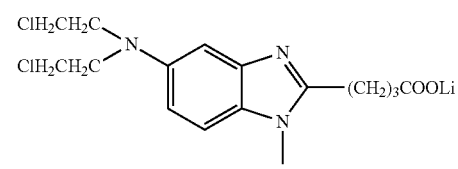
(V)

comprising hydrolyzing the compound of formula (IV), wherein R is $C_1$-$C_6$ alkyl with a lithium source

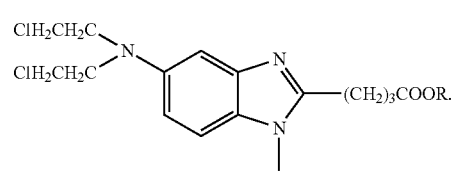
(IV)

A fourth aspect of the present invention provides an improved process for preparation of bendamustine hydrochloride of the formula (VI)

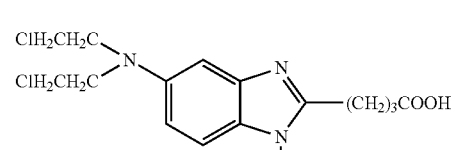
(VI)

comprising reacting a compound of the formula (II)

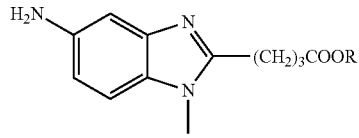
(II)

with a 2-haloethanol in the presence of calcium carbonate to obtain compound of formula (III)

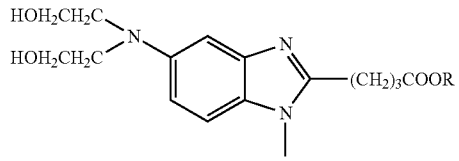
(III)

and converting the compound of formula (III) to bendamustine hydrochloride of formula (VI).

DESCRIPTION OF THE DRAWINGS AND FIGURES

DETAILED DESCRIPTION OF THE INVENTION

Figure 1:
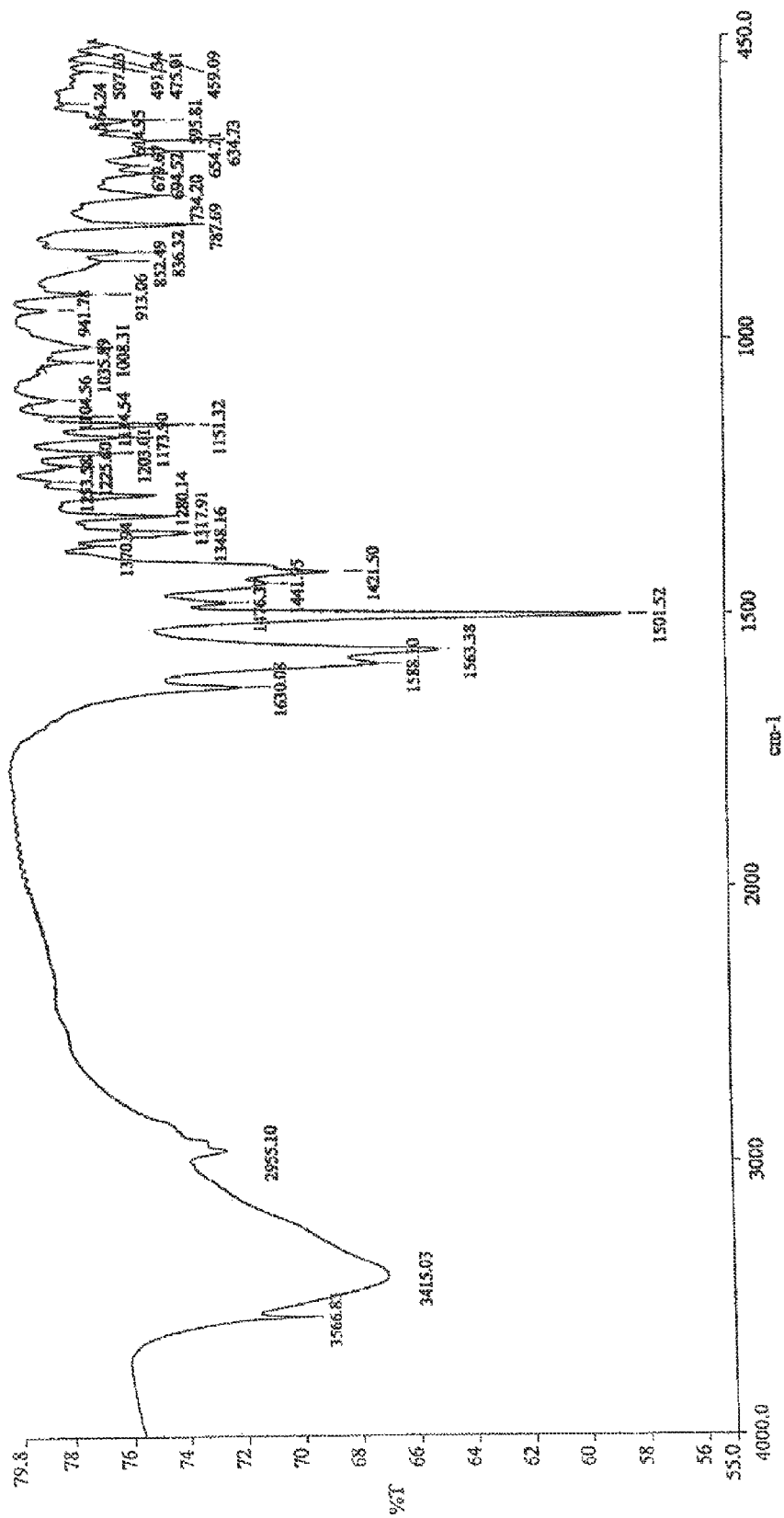
FIG. 1 is a representative infrared spectrum of lithium 4-[1-methyl-5-bis-(2-chloroethyl)-benzimidazolyl-2]butanoate (V), obtained by the process of the present invention.
Figure 2:
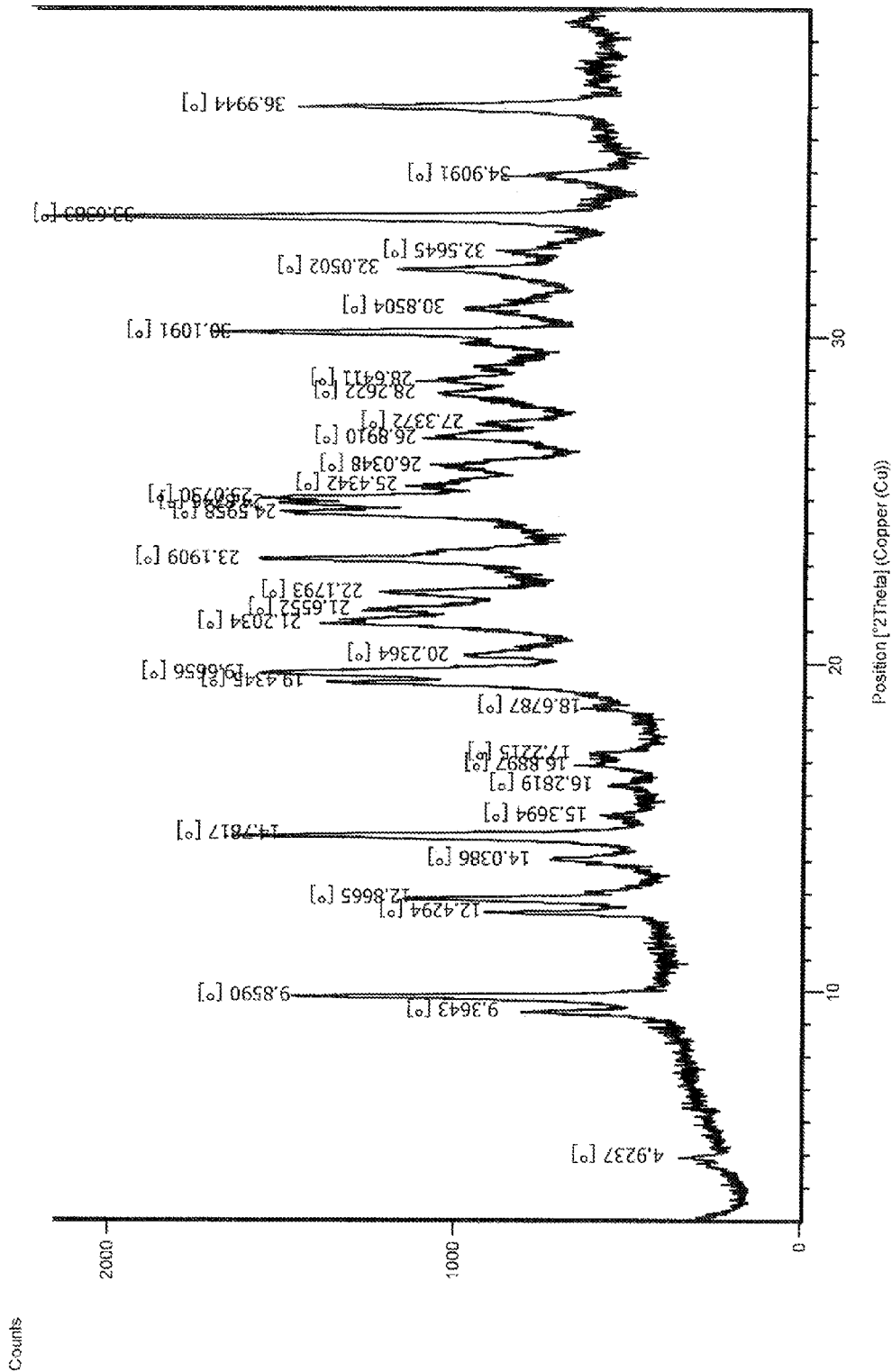
FIG. 2 is a representative X-Ray (powder) Diffraction Pattern (XRPD) of lithium 4-[1-methyl-5-bis-(2-chloroethyl)-benzimidazolyl-2] butanoate (V), obtained by the process of the present invention.

Embodiments of the application relate to the preparation of bendamustine hydrochloride. Those skilled in the art will recognize that the process can easily be modified to prepare other salts of bendamustine.

A first aspect of the present invention provides an improved process for the preparation of bendamustine hydrochloride of formula (VI)

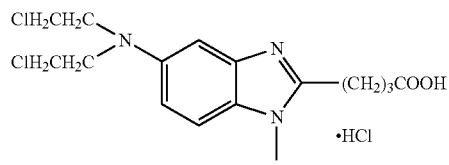
(VI)

comprising the steps of:

a) reacting a compound of the formula (II), wherein R is $C_1$-$C_6$ alkyl

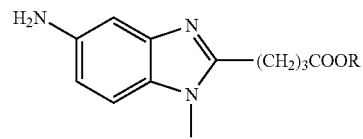
(II)

with a 2-haloethanol in the presence of a base to give a compound of formula (III);

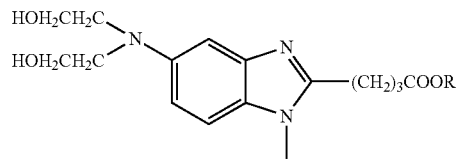
(III)

b) reacting the compound of formula (III) with a chlorinating agent to provide a compound of formula (IV);

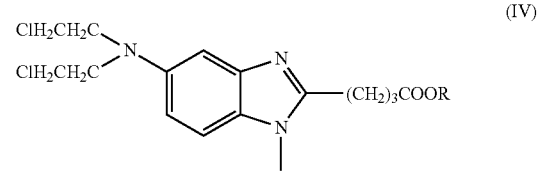
(IV)

c) hydrolyzing the compound of formula (IV) with lithium hydroxide to give a compound of formula (V); and

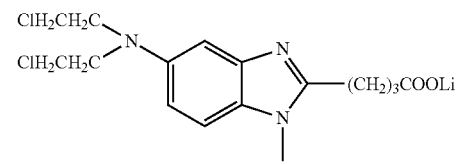
(V)

d) converting the compound of formula (V) to bendamustine or bendamustine hydrochloride of formula (VI)

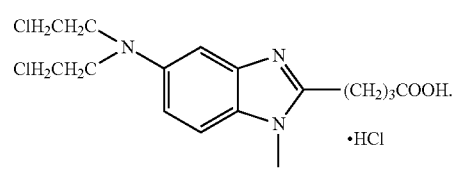
(VI)

Steps for this process are separately described in detail below.

Step a) involves reacting a compound of formula (II) with a 2-haloethanol in the presence of a base to give a compound of formula (III).

The starting compound of formula (II) may be obtained by known processes including the process disclosed by Li-Mei et al., in Zhongguo Xinyao Zazhi (2007), 16(23), 1960-1961, 1970. 2-haloethanol compounds that may be used in the processes of the present invention include 2-chloroethanol, 2-bromoethanol, 2-iodoethanol, or the like. The most preferred is 2-bromoethanol.

Typically, 2-bromoethanol is employed in proportions of between 2.0 to 10.0 moles per molar equivalent of the compound of formula (II), preferably in proportions of between 2.0 to 4.0 moles per molar equivalent of the compound of formula (II), and more preferably in proportions of between 2.0 to 3.0 moles per mole of per molar equivalent of the compound of formula (II).

The base used in step a) may be an inorganic base or an organic base. Inorganic bases such as potassium carbonate, sodium carbonate, calcium carbonate, sodium hydroxide, potassium hydroxide or the like may be used as the base in step a). The most preferred inorganic base is calcium carbonate.

The inventors of the present application have found that use of an inorganic base, e.g., potassium carbonate, in the above step as per the prior art process results in the formation of a tri-hydroxy impurity of the formula (VII), which leads to lower yield, and the product was obtained as a gummy mass. Furthermore, when potassium carbonate was used for step a) the purity of the product obtained was found to be not more than 80% by HPLC.

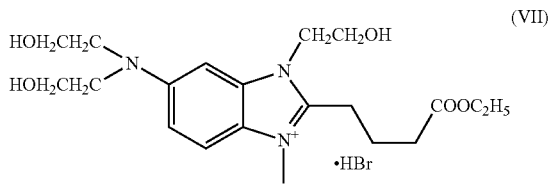

It was surprisingly found that by using calcium carbonate in place of potassium carbonate, the product was obtained in higher yield and a purity of greater than about 95% and with minimum amounts of the other undesired side products. The purity of the compound of formula (III) was found to be greater than 97%.

The organic base may be selected from the group comprising of $C_1$-$C_4$ alkyl ammonia; mono, di or tri $C_1$-$C_4$ alkyl amine such as triethyl amine, diisopropyl ethyl amine; mono, di or tri hydroxy $C_1$-$C_4$ alkyl amine; morpholine; thiomorpholine; piperidine; and pyrrolidine.

The reaction of step a) may be carried out in the presence of a solvent. Useful solvents include, without limitation thereto, water; nitriles solvents such as acetonitrile or propionitrile; alcohols, such as methanol, ethanol and isopropanol; chlorinated hydrocarbons, such as methylene chloride, ethylenedichloride; dipolar aprotic solvents, such as dimethylsulfoxide and dimethylformamide; esters, such as ethyl acetate and isopropyl acetate; cyclic ethers, such as dioxane and tetrahydrofuran; and mixtures thereof. The most preferred solvent is acetonitrile.

The reaction may be carried out at temperatures ranging from about 25° C. to about 100° C., preferably from about 80° C. to about 90° C. After completion of the reaction, the compound of the formula (III) is isolated and may be purified to obtain a solid having a purity of greater than 97% by HPLC.

Step b) involves reacting the compound of formula (III) with a chlorinating agent, to give a compound of formula (IV). Chlorinating agents that may be used include, but are not limited to: sulfur-based chlorinating agents such as sulfuryl chloride, thionyl chloride, or the like; and phosphorous-based chlorinating agents such as phosphorous trichloride, phosphorous pentachloride, phosphorous oxychloride, or the like.

Typically, the amounts of chlorinating agent may be employed in proportions of between 2.0 to 6.0 moles per molar equivalent of the compound of formula (III), preferably in proportions of between 2.0 to 4.0 moles per molar equivalent of the compound of formula (III), and more preferably in proportions of between 2.0 to 2.5 moles per molar equivalent of the compound of formula (III).

The process may be carried out in the presence of a solvent, such as a halogenated hydrocarbon, e.g., 1,2-dichloroethane, dichloromethane, chloroform, or the like. The reaction may be carried out at temperatures ranging from about 0° C. to about 50° C., preferably from about 25° C. to about 45° C. and more preferably from 35° C. to 45° C. In a particular embodiment, the compound of formula (III) is reacted with thionyl chloride in the presence of dichloromethane, to give a compound of formula (IV).

The purity of the compound of the formula (IV) as a solid has been found to be greater than 98% by HPLC. In a particular embodiment, the purity has been found to be more than 99% by HPLC.

Most of the known processes for the preparation of bendamustine hydrochloride do not involve isolation of the compound of formula (IV), and involve direct in situ conversion or involve the conversion of the concentrated reaction mass obtained by distillation to bendamustine hydrochloride. This may result in carrying forward the process impurities, thereby decreasing the yield and purity of the final product.

Therefore, isolating the compound of formula (IV) as a solid and its optional purification are features of embodiments of the present application. The process for isolating the compound of formula (IV) as disclosed in the present application results in improved color, yield, and purity of the product.

Step c) involves the hydrolysis of the compound of formula (IV). Step c) may be carried out in a very mild basic medium at ambient temperature in organic solvent to give a compound of the formula (V). The lithium source may be selected from the group comprising of lithium hydroxide, lithium carbonate, lithium hydride and the like. The hydrolysis of the compound of the formula (IV) may be carried out using a solution of lithium hydroxide hydrate (LiOH.H$_2$O) in water. At ambient temperature, use of other inorganic bases such as potassium carbonate or potassium hydroxide result in either an incomplete reaction or isolation of a sticky material having quite reduced purity.

Typically, lithium hydroxide monohydrate is employed in proportions of between 2.0 to 4.0 moles per mole of the compound of formula (IV) and preferably in proportions of between 2.0 to 3.0 moles per mole of the compound of formula (IV).

The reaction of step c) may be carried out in the presence of a solvent. Useful solvents include, without limitation thereto, ketones such as acetone, methyl ethyl ketone, isobutyl ketone; water; nitriles such as acetonitrile or propionitrile; alcohols, such as methanol, ethanol and isopropanol; chlorinated hydrocarbons, such as methylene chloride, ethylenedichloride; dipolar aprotic solvents, such as dimethylsulfoxide and dimethylformamide; esters, such as ethyl acetate and isopropyl acetate; cyclic ethers, such as dioxane and tetrahydrofuran; and mixtures thereof. The most preferred solvent is acetone or a mixture of acetone with water.

Step d) involves the conversion of compound of formula (V) into compound of formula (VI) i.e., bendamustine hydrochloride. Step d) may be carried out by dissolving the compound of formula (V) in acid below room temperature.

The acid used in Step d) may include mineral acids such as aqueous hydrochloric acid, aqueous sulfuric acid, aqueous phosphoric acid, aqueous perchloric acid, aqueous hydrobromic acid, or carriers containing an acid such as acidic resins. The most preferred acid is conc. hydrochloric acid.

Conc. HCl may be employed in proportions of 1 to 4 times by volume of the amount of the compound of formula (V) employed, preferably in proportions of 1 to 3 times by volume of the amount of the compound of formula (V) employed and more preferably in proportions of 1 to 2 times by volume of the amount of the compound of formula (V) employed.

Demineralised (DM) water may be employed in proportions of 5 to 20 times by volume of the amount of the compound of formula (V) employed, preferably in proportions of 5 to 15 times by volume of the amount of the compound of formula (V) employed and more preferably in proportions of 5 to 10 times by volume of the amount of the compound of formula (V) employed.

The bendamustine hydrochloride obtained is of more than 99.8% chromatographic purity by HPLC.

Bendamustine hydrochloride (VI), as mentioned hereinbefore, is obtained in a purity of ≥99.5% having undesired impurities at RRT-0.46, RRT-1.27 and RRT-1.31 as per regulatory requirements i.e. less than 0.1% determined by HPLC. The bendamustine hydrochloride, thus obtained, as per the method of the present invention, is crystalline in nature.

Known processes for the preparation of bendamustine hydrochloride most often use temperatures higher than room temperature. Preparing bendamustine hydrochloride at higher temperature results in the formation of impurities at RRT 0.46, RRT 1.27 and RRT 1.31 in higher quantity as compared when hydrochloride formation is done at room temperature or below it.

It was found that by carrying out the hydrolysis of compound of the formula (IV) (i.e., 4-[1-methyl-5-bis-(2-chloroethyl)-benzimidazolyl-2]butyric acid ethyl ester) in mild alkaline medium (e.g., using an aqueous solution of lithium hydroxide hydrate solution instead of acidic medium) and isolating lithium salt of 4-[1-methyl-5-bis-(2-chloroethyl)-benzimidazolyl-2]butyric acid (V) followed by conversion to bendamustine hydrochloride (VI) in conc. HCl instead of directly isolating bendamustine hydrochloride (VI) from the compound of formula (IV), a very significant reduction in the formation of undesired impurities at RRT 0.46, RRT 1.27 and RRT 1.31 could be achieved. The amount of the undesired impurities at RRT 0.46, RRT 1.27 and RRT 1.31 was found to be less than 0.1%, determined by HPLC as compared to more than 0.1%, or more than 0.5% in some cases, formed by the prior art methods as determined by HPLC. The amount of the undesired impurities at RRT 0.46, RRT 1.27 and RRT 1.31 are in compliance with regulatory requirements i.e., less than 0.10% limit of unknown impurities determined by HPLC. The removal of impurities at RRT 0.46, RRT 1.27 and RRT 1.31 requires successive purifications or tedious chromatography which needless to mention, is not only tedious but also results in significant yield loss.

A comparison of the purity of bendamustine hydrochloride and impurities at RRT 0.46, RRT 1.27 and RRT 1.31 by the method of the present invention for the preparation of bendamustine through carrying out the hydrolysis of the compound of the formula (IV) in mild alkaline medium and isolating lithium salt and its conversion to bendamustine hydrochloride and a prior art method is summarized in Table-1:

TABLE 1

Comparison of The Method of The Present Invention for Preparation of Bendamustine Hydrochloride through Present Invention vs Reported Method

| Reference | Bendamustine Hydrochloride | Impurity at RRT 0.46 | Impurity at RRT 1.27 | Impurity at RRT 1.31 |
|---|---|---|---|---|
| DD159877 | 99.05% | 0.57% | 0.22% | 0.13% |
| | 98.96% | 0.73% | 0.08% | 0.16% |
| Present Invention | 99.80% | 0.02% | Not Detected | Not Detected |
| | 99.74% | 0.06% | | 0.04% |

From the comparison given in Table-I, the advantages and superiority of the method of the present invention over the prior art methods is highly evident. The method of the present invention is simple, convenient and economical and most importantly, does not take recourse to any multiple and tedious isolation method and strict adherence to critical reaction conditions and parameters for the preparation and isolation of lithium salt of 4-[1-methyl-5-bis-(2-chloroethyl)-benzimidazolyl-2]butyric acid (V) and bendamustine hydrochloride (VI).

A second aspect of the present invention provides a compound of the formula (V):

| Functional Groups | Wave Numbers ( ) in cm$^{-1}$ |
|---|---|
| O—H Stretching | 3415.03 |
| C—H Stretching, aliphatic | 2955.10 |
| N—CH$_3$ Stretching | 1501.52 |
| C═C Stretching, aromatic | 1630.08 | which is a useful intermediate for the preparation of highly purified bendamustine hydrochloride.

The compound of the formula (V) may be characterized by the following spectroscopic data:

A) Infrared Spectrum: IR spectrum in KBr was recorded on Perkin Elmer, Spectrum 100FT-IR spectrometer.

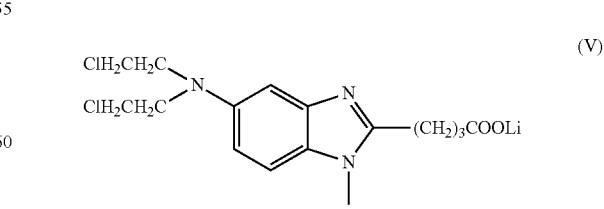

(V)

B) $^1$H Nuclear Magnetic Resonance (NMR) Spectrum: $^1$H and $^{13}$C NMR spectra were recorded on a Varian 400 MHz NMR spectrometer using DMSO as the solvent.

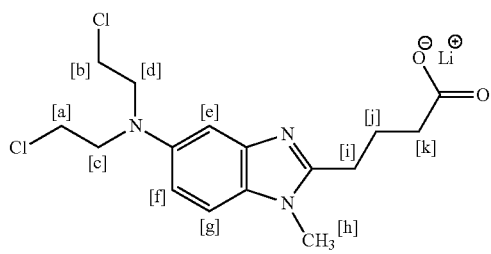

| Chemical Shift (ppm) | No. of Protons | Splitting Pattern | Position of Protons |
|---|---|---|---|
| 1.821-1.856 | 2 | m | J |
| 1.961-1.994 | 2 | t | K |
| 2.745-2.782 | 2 | T | I |
| 3.662 | 3 | s | H |
| 3.691 | 8 | | a, b, c, d |
| 6.753-6.774 | 1 | d, (J = 8.4 Hz) | F |
| 6.898 | 1 | s | E |
| 7.290-7.311 | 1 | d, (J = 8.4 Hz) | g |

C) $^{13}$C Nuclear Magnetic Resonance (NMR) Spectrum:

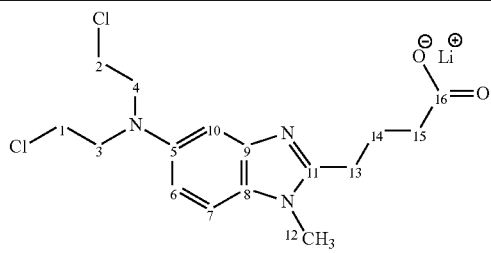

| Chemical Shift (ppm) | Position of Carbons |
|---|---|
| 24.701 | 13 |
| 26.769 | 14 |
| 29.634 | 15 |
| 37.603 | 12 |
| 41.662 | 1, 2 |
| 53.759 | 3, 4 |
| 102.457 | 10 |
| 110.108 | 6 |
| 110.318 | 7 |
| 129.439 | 8 |
| 142.458 | 9 |
| 143.472 | 5 |
| 155.972 | 11 |
| 177.231 | 16 |

D) Mass Spectrometer (MS)

Mass spectrum of the bendamustine intermediate (i.e., the compound of the formula (V)) was recorded on a QTRAP 3200 mass spectrometer in ESI$^+$ mode.

| Peak | m/z | Mode |
|---|---|---|
| [M + H]$^+$ | 356.2, 358.1, 360.1 | ESI$^+$ |

A third aspect of the present invention provides a process for the preparation of Lithium salt of 4-[1-methyl-5-bis-(2-chloroethyl)-benzimidazolyl-2]butyric acid of formula (V)

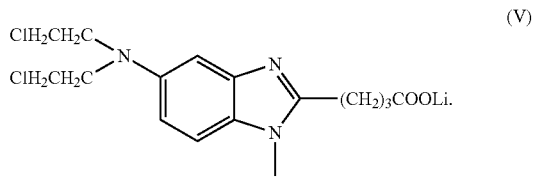

comprising hydrolyzing the compound of formula (IV), wherein R is $C_1$-$C_6$ alkyl with lithium hydroxide

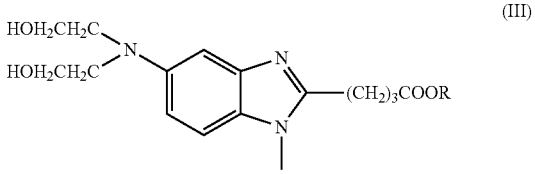

The detailed description of the third aspect is the same as step c) of first aspect of the present invention.

A fourth aspect of the present invention provides an improved process for preparation of compound of formula (VI)

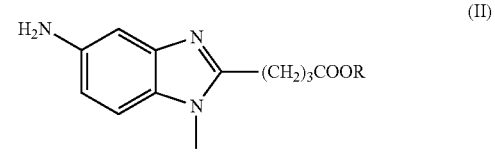

comprising reacting a compound of the formula (II)

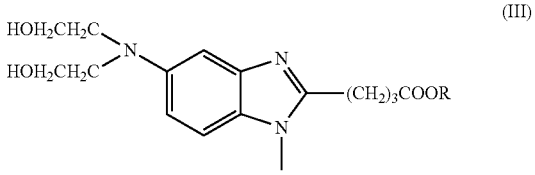

with a 2-haloethanol in the presence of calcium carbonate to obtain a compound of formula (III)

(III)

HOH$_2$CH$_2$C\\
HOH$_2$CH$_2$C／N—[benzimidazole]—(CH$_2$)$_3$COOR and converting the compound of formula III to bendamustine hydrochloride of formula VI.

The detailed description of the fourth aspect is the same as that of first aspect of the present invention.

Isolation of the intermediates in the solid form (i.e., the compounds of the formula (III), (IV) and (V)) has the following advantages, as compared to the known processes:

a) It primarily achieves a significant reduction in the amount of the undesired impurities formed at RRT 0.46, RRT 1.27 and RRT 1.31, which are formed in significant amounts by the methods disclosed in the prior art methods;

b) It overcomes the problems of isolation of the compound of the formula (III) and (IV) as solids, as compared to various processes known in the prior art where a gummy or oily mass is attained;

c) Isolation of the intermediates compound of formula (III) and (IV) as solids facilitates their purification which results in their improved purity and easily conversion to bendamustine hydrochloride of Pharmacopoeial Grade;

d) Isolation of the novel intermediate of the formula (V) results in the significant removal of the impurities at RRT 0.46, RRT 1.27 and RRT 1.31, which results in the isolation of highly purified bendamustine hydrochloride without any further purification;

e) It requires milder conditions for the formation of the novel intermediate of the formula (V);

f) It requires milder conditions and temperatures less than ambient temperature for the conversion of the compound of formula (V) into bendamustine hydrochloride.

g) Synthesis of bendamustine hydrochloride through isolation of the intermediate of the formula (V) results in higher purity of bendamustine hydrochloride without the need of any further purification.

The process for preparation of bendamustine hydrochloride as per the present invention is further exemplified by way of the following examples, which, in no way should be construed as limiting the scope of the invention.

Reference Example-1

Preparation of Bendamustine Hydrochloride as per Patent No. DD159877

Ethyl 4-[1-methyl-5-bis-(2-hydroxyethyl)-amino-benzimidazolyl-2]butanoate (4, 4.305 g) was added to chloroform (36 mL) and agitated until a clear solution was formed. The solution was cooled to 0° C. Thionyl chloride (2.175 g) was added to the above solution within 40 minutes, maintaining the temperature of the solution to 0-5° C. by cooling. The reaction mixture was agitated at 0-5° C. for 1 hour. The temperature was raised slowly to room temperature by removing cooling within 2.5 to 3 hrs and subsequently agitated at room temperature for 15 to 16 hrs. The solution was dispersed by agitating in 37.5 mL concentrated hydrochloric acid whereby excess thionyl chloride was decomposed under increased hydrochloric acid and $SO_2$ development. The chloroform was distilled away and further stirred for 3 hrs at around 95° C. Activated carbon (0.78 g) was added to the solution and stirred for further 30 minutes at around 95° C. The solution was concentrated to almost 8 mL under vacuum and the residue was diluted with 24 mL of water and stirred up to crystallization. The further purification was done by recrystallization from water.

Example-1

Preparation of Ethyl 4-[5-[bis(2-hydroxyethyl) amino]-1-methyl-1H-benzimidazol-2-yl]butanoate (III)

Ethyl 4-(5-amino-1-methyl-1H-benzimidazol-2-yl)butanoate (II, 40.0 g, 0.153 mol) was added to 2-bromoethanol (80 mL) and agitated for 15-30 minutes. Acetonitrile (80 mL) and calcium carbonate (61.3 g, 0.61 mol) were added to the reaction mixture. The reaction mixture was heated to 80-90° C. within 2 hours and refluxed at 80-90° C. for 34-38 hours. The reaction mixture was cooled to below 70° C. and acetonitrile (80.0 mL) was added. The reaction mixture was further cooled to 20-30° C. and filtered through celite prewashed with acetonitrile. The filtrate was concentrated at 50-60° C. under vacuum until a viscous mass was obtained.

The viscous mass was cooled to 20-30° C. Dichloromethane (320.0 mL) was added to the viscous mass under stirring and washed with potassium carbonate solution (32.0 g in 200 mL water). The organic layer was washed with DM water twice. The organic layer (dichloromethane) was concentrated under vacuum at 35-40° C. until a viscous mass was obtained. The viscous mass was dried under vacuum at 35-40° C. for one hour. Ethyl acetate (160.0 mL) was added to the viscous mass and cooled to 0-5° C. and stirred for one hour. The solid separated out was filtered and washed with ethyl acetate. The isolated solid was dissolved in dichloromethane and concentrated the solution under vacuum at 35-40° C. to obtain a viscous mass. The viscous mass was dissolved in acetone and cooled to 0-5° C. under stirring. The solid separated out was filtered, washed with acetone and dried at 40-45° C. under vacuum for 4-6 hours to give the title compound (III, 30.1 g; 56.30%), with a purity of 97.22%.

Example-2

Preparation of Ethyl 4-[5-[bis(2-chloroethyl)amino]-1-methyl-1H-benzimidazol-2-yl]butanoate (IV)

4-[5-[bis(2-hydroxyethyl)amino]-1-methyl-1H-benzimidazol-2-yl]butanoate (III, 90.0 g, 1.15 mole) was added to dichloromethane (6.24 L) and agitated until a clear solution was formed. A solution of thionyl chloride (292.3 g, 2.52 mol) in dichloromethane (1.56 L) was added slowly in 2 to 3 hours. After complete addition of thionyl chloride solution, reaction mixture was refluxed at 35-45° C. for 6 hours. The reaction mixture was cooled to 20-30° C. and 1.95 L dichloromethane was added. A potassium carbonate solution (351.0 g in 1.95 L water) was added to the reaction mixture slowly to control the evaluation of effervescence. The layers were separated. The organic (dichloromethane) layer was washed with brine solution. The organic layer was concentrated at 30-35° C. under vacuum until a viscous mass was obtained. The viscous mass was dissolved in acetone (1.95 L) and DM water (1.365 L) was slowly. The resulting mixture was stirred at 20-30° C. for one hour followed by cooling to 0-5° C. The solid separated out was washed with a chilled mixture of acetone (390 mL) and DM water (195.5 mL) twice. The material was dried and used in the next step of the reaction without further purification.

Example-3

Preparation of Lithium 4-[1-methyl-5-bis-(2-chloroethyl)-benzimidazolyl-2] butanoate (V)

Ethyl 4-[1-methyl-5-bis-(2-chloroethyl)-benzimidazolyl-2]butanoate (IV, 980.0 g, 0.983 mol) was added to acetone (9.5 L) and agitated until completely dissolved. The solution was cooled to 15-20° C. A solution of $LiOH.H_2O$ (103.18 g, 2.46 mol) in water (1.9 L) was prepared and added slowly in 6 to the above solution (IV in acetone) in 15 to 30 minutes maintaining the temperature of reaction mixture to 15-20° C. The mixture was maintained at a temperature of 15-20° C. for 6 hours under agitation. After completion of the reaction, the reaction mixture was cooled to 0-5° C. and maintained at a temperature of 0-5° C. for one hour under agitation. The solid precipitated was filtered and dried for 15-20 minutes.

The dried solid was added to chilled (0-5° C.) (1:1 mixture) acetone: DM water (100.0 mL) and agitated at a temperature of 0-5° C. for 5-10 minutes. The solid was filtered and washed with acetone (760.0 mL each X 2=1.52 L) at 20-25° C. and dried.

The dried solid was added to acetone (3.8 L) at 20-25° C. and maintained at a temperature of 20-25° C. for 20-30 minutes under agitation. The solid was filtered and washed with acetone (380.0 mL each X 2=760.0 mL) at 20-25° C. and dried for one hour.

The above dried solid was added to acetone (11.4 L) at 20-25° C. and heated the mixture to reflux at 55-60° C. The reaction mixture was maintained at a temperature of 55 to 60° C. for 2-3 hours under agitation. The mixture was cooled to 35-40° C. The solid was filtered and washed with acetone (760.0 mL each X 2=1.52 L) and dried at 40-45° C. under 0-10 mbar vacuum for 4-6 hours to give the title compound (V, 310.0 g; 86.53%), with a purity of 99.52%.

Example-4

Preparation of Bendamustine hydrochloride (VI) through Lithium 4-[1-methyl-5-bis-(2-chloroethyl)-benzimidazolyl-2] butanoate (V)

Activated charcoal (11.0 g) was added to Conc. HCl (165.0 mL) under stirring and cooled to 5-10° C. Lithium 4-[1-methyl-5-bis-(2-chloroethyl)-benzimidazolyl-2] butanoate (V, 110.0 g, 0.302 mol) was added below 65° C. under agitation and agitated for 30-45 minutes. The reaction mass was filtered on celite bed prewashed with conc. HCl and the celite bed was washed with conc. HCl (27.5 mL). The filtrate and washings were combined. DM water (550.0 mL) was added to combined filtrate and washings and agitated for 15 minutes. DM water (1.1 L) was added and stirred at 20-30° C. for 30 minutes. The resulting mass was cooled to 0-5° C. and maintained at a temperature of 0 to 5° C. for 30 minutes under agitation. The solid was filtered, washed with chilled (0-5° C.) DM water twice (220.0 mL each X 2=440.0 mL) followed by with chilled acetone (0-5° C.) (55.0 mL) and sucked dried for 1 hour. The solid cake was agitated with acetone (1100 OmL) for 10 minutes and filtered. The solid material was dried at 20-25° C. under 100-200 mbar vacuum for one hour to obtain a moisture content of between 4.4-6.0% w/w to give the title compound (VI, 80.0 g; 67.10%), with a purity of 99.86%.

Example-5

Preparation of Ethyl 4-[5-[bis(2-hydroxyethyl) amino]-1-methyl-1H-benzimidazol-2-yl]butanoate (III)

Ethyl 4-[5-amino-1-methyl-1H-benzimidazol-2-yl)butanoate (II, 200.0 g, 0.763 mol) was added to DM Water (1.1 L). Aqueous sodium acetate.3H$_2$O (20.0 g sodium acetate.3H$_2$O in 100 mL DM water) and acetic acid (400 mL) was added and agitated until complete dissolution of compound of the formula II. The reaction mixture was cooled to 0-5° C. and ethylene oxide (270.0 g, 6.12 mole) was added maintaining the temperature of the reaction mixture at 0-5° C. The reaction mixture was stirred at 0-5° C. for 5 hours. The temperature of reaction mixture was raised to 20-25° C. and agitated at 20-25° C. for 18 hours. After completion of the reaction, dichloromethane (2.0 L) was added at 20-25° C. followed by addition of aqueous solution of potassium carbonate (440.0 g potassium carbonate in 1.1 L DM water) portion wise at 20-25° C. to control the evaluation of effervescence and agitated at 20-25° C. for 5-10 minutes. The layers were separated. The organic layer (dichloromethane) was washed with DM water (1.0 L) twice and organic layer was concentrated under vacuum at 40-50° C. until a viscous mass was obtained. The viscous mass was dissolved in acetone (1.0 L), cooled to 0-5° C. and agitated at 0-5° C. for 1 hour. The solid separated out was filtered, washed with chilled (0-5° C.) acetone (200.0 mL) and dried at 40-50° C. under vacuum for 6 hours to give the title compound (III, 210.0 g; 78.53%), with a purity of 99.06%.

We claim:

1. A process for preparing bendamustine or bendamustine hydrochloride of formula (VI)

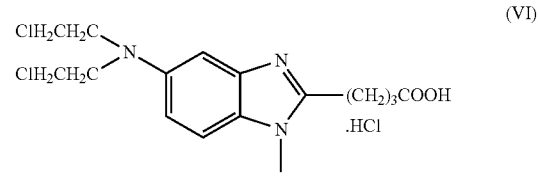

the process comprising:

a) reacting a compound of formula (II), wherein R is $C_1$-$C_6$ alkyl,

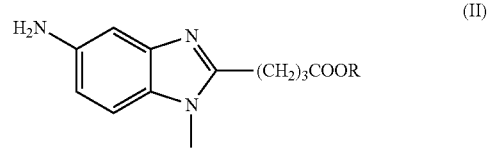

with 2-haloethanol in the presence of calcium carbonate and a solvent to give a compound of formula (III), wherein the solvent comprises acetonitrile; propionitrile; methanol; ethanol; isopropanol; 1,2-dichloroethane; dichloromethane; chloroform dimethylsulfoxide; dimethylformamide; ethyl acetate; isopropyl acetate; dioxane; tetrahydrofuran; or a mixture thereof;

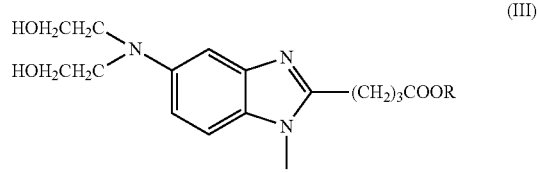

b) reacting the compound of formula (III) with a chlorinating agent in the presence of a solvent to provide a compound of formula (IV);

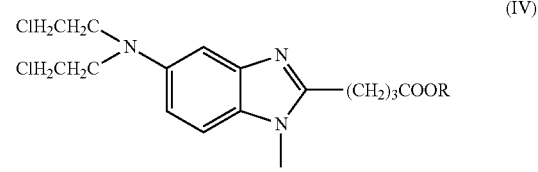

c) hydrolyzing the compound of formula (IV) with a lithium source in the presence of a solvent to give a compound of formula (V); and

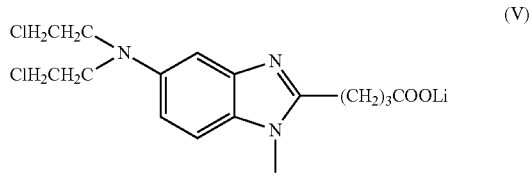
(V)

d) converting the compound of formula (V) to bendamustine or bendamustine hydrochloride of Formula VI.

2. The process according to claim 1, wherein the 2-haloethanol is selected from the group consisting of 2-chloroethanol, 2-bromoethanol and 2-iodoethanol.

3. The process according to claim 1, wherein the chlorinating agent is sulfuryl chloride; thionyl chloride; phosphorous trichloride; phosphorous pentachloride; or phosphorous oxychloride.

4. The process according to claim 1, wherein the solvent used for the reaction of the compound of formula (III) with a chlorinating agent is selected from the group consisting of 1,2-dichloroethane, dichloromethane, and chloroform.

5. The process according to claim 1, wherein the purity of the compound of formula (IV) is greater than 99%.

6. The process according to claim 1, wherein the lithium source is selected from the group consisting of lithium hydroxide hydrate, lithium carbonate and lithium hydride.

7. The process according to claim 1, wherein hydrolysis of the compound of formula (IV) is carried out in the presence of lithium hydroxide hydrate in water.

8. The process according to claim 1, wherein the solvent used in hydrolysis of the compound of formula (IV) is water; acetone; methyl ethyl ketone; isobutyl ketone; acetonitrile; propionitrile; methanol; ethanol; isopropanol; methylene chloride; ethylenedichloride; dimethylsulfoxide; dimethylformamide; ethyl acetate; isopropyl acetate; dioxane; tetrahydrofuran; or a mixture thereof.

9. The process according to claim 8, wherein the solvent is acetone or a mixture of acetone and water.

10. The process according to claim 1, wherein the conversion of the compound of formula (V) into bendamustine or bendamustine hydrochloride is carried out by dissolving the compound of formula (V) in acid at or below room temperature.

11. The process according to claim 10, wherein the acid is a mineral acid selected from the group consisting of aqueous hydrochloric acid, aqueous sulfuric acid, aqueous phosphoric acid, aqueous perchloric acid, and aqueous hydrobromic acid, or wherein the acid is an acidic resin.

12. The process according to claim 1, wherein the conversion of the compound of formula (V) into bendamustine hydrochloride of formula (VI) is carried out by dissolving the compound of formula (V) in hydrochloric acid at or below room temperature.

13. The process according to claim 1, wherein the purity of the bendamustine hydrochloride of formula (VI) is greater than 99.8%.

14. The process according to claim 1, wherein the bendamustine hydrochloride of formula (VI) has less than about 0.10% of the following impurities:

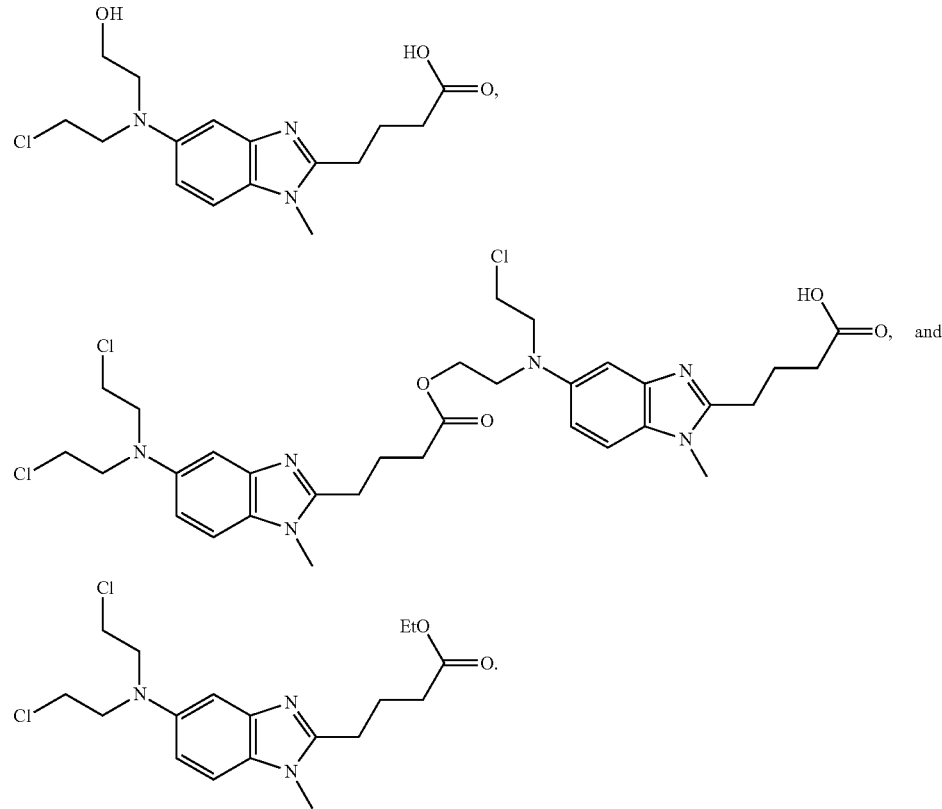

15. The process according to claim 1, wherein the 2-haloethanol is 2-bromoethanol.

16. The process according to claim 1, wherein the chlorinating agent is thionyl chloride or phosphorous oxychloride.

17. The process according to claim 1, wherein the lithium source is lithium hydroxide hydrate.

18. The process according to claim 1, wherein the solvent used for the reaction of the compound of the formula (II) with 2-haloethanol is acetonitrile.

19. The process according to claim 1, wherein the solvent used for the reaction of the compound of formula (III) with a chlorinating agent is dichloromethane.

20. The process of claim 1, wherein the obtained bendamustine hydrochloride of formula (VI) has an impurity at RRT 0.46, RRT 1.27 and RRT 1.131 in an amount less than about 0.10-area %.

21. The process of claim 1, wherein the obtained bendamustine hydrochloride of formula (VI) has an impurity at RRT 0.46 in an amount less than about 0.10-area %.

22. The process of claim 1, wherein the obtained bendamustine hydrochloride of formula (VI) has an impurity at RRT 1.27 in an amount less than about 0.10-area %.

23. The process of claim 1, wherein the obtained bendamustine hydrochloride of formula (VI) has an impurity at RRT 1.131 in an amount less than about 0.10-area %.

24. The process of claim 1, further comprising isolating the compound of formula (III) prior to step b) as a solid.

25. The process of claim 1, further comprising isolating the compound of formula (IV) prior to step c) as a solid.

26. The process of claim 1, further comprising isolating the compound of formula (V) prior to step d) as a solid.

27. The process of claim 1, wherein the solvent used for the reaction of the compound of formula (II) with 2-haloethanol further comprises water.

* * * * *